United States Patent [19]

Bozeman, Jr.

[11] Patent Number: 5,458,655
[45] Date of Patent: Oct. 17, 1995

[54] CONTROL METHOD FOR PROSTEHETIC DEVICES

[75] Inventor: Richard J. Bozeman, Jr., Dickinson, Tex.

[73] Assignee: The United States of America as represented by the United States, National Aeronautics and Space Administration, Washington, D.C.

[21] Appl. No.: 283,474

[22] Filed: Jul. 26, 1994

Related U.S. Application Data

[62] Division of Ser. No. 937,325, Aug. 31, 1992, Pat. No. 5,376,128.

[51] Int. Cl.$^6$ .................................. A61F 2/54; A61F 2/70
[52] U.S. Cl. .................................. 623/24; 623/58; 623/63
[58] Field of Search .................................. 623/24, 25, 58, 623/63, 64, 62, 60

[56] References Cited

U.S. PATENT DOCUMENTS

| | | | |
|---|---|---|---|
| 3,609,769 | 10/1971 | Suzuki et al. | 623/24 |
| 3,866,246 | 2/1975 | Seamone et al. | 623/24 |
| 4,067,070 | 1/1978 | Seamone et al. | 623/60 X |

Primary Examiner—David H. Willse
Attorney, Agent, or Firm—Hardie R. Barr

[57] ABSTRACT

A control system and method for prosthetic devices is provided. The control system comprises a transducer for receiving movement from a body part for generating a sensing signal associated with that movement. The sensing signal is processed by a linearizer for linearizing the sensing signal to be a linear function of the magnitude of the distance moved by the body part. The linearized sensing signal is normalized to be a function of the entire range of body part movement from the no-shrug position of the moveable body part through the full-shrug position of the moveable body part. The normalized signal is divided into a plurality of discrete command signals. The discrete command signals are used by typical converter devices which are in operational association with the prosthetic device. The converter device uses the discrete command signals for driving the moveable portions of the prosthetic device and its sub-prosthesis. The method for controlling a prosthetic device associated with the present invention comprises the steps of receiving the movement from the body part, generating a sensing signal in association with the movement of the body part, linearizing the sensing signal to be a linear function of the magnitude of the distance moved by the body part, normalizing the linear signal to be a function of the entire range of the body part movement, dividing the normalized signal into a plurality of discrete command signals, and implementing the plurality of discrete command signals for driving the respective moveable prosthesis device and its sub-prosthesis.

13 Claims, 5 Drawing Sheets

CONTROL METHOD FOR PROSTEHETIC DEVICES

This is a division, of application Ser. No. 07,937,325, filed Aug. 31, 1992, now U.S. Pat. No. 5,376,128.

BACKGROUND OF THE INVENTION

1. Field of the Invention

The present invention relates to a control system and associated method for use with prosthetic devices. Particularly, the present invention relates to a prostheses control system and method for below-the-elbow amputees.

2. Description of the Prior Art

Typically, a prostheses aims to give relief to persons disabled by the absence or defect in their body parts. The field of prostheses has most advanced in the area of artificial arms and artificial legs. In particular, artificial arms are required to produce complicated motions. A high degree of perfection has been reached with respect to the use of electric motors and hydraulic drives for operating such artificial arms and legs. The control of a drive mechanism in association with a prosthesis calls for highly complicated processing. Various methods have previously been used and proposed for the purpose of such control.

Much work has been done in the field of prosthetic devices. Prior art devices include the hook and cable system developed in the 1800's and still used today. Hydraulic actuated prostheses and computer controlled "bionic" type devices are available. The disadvantages of prior devices range from only two digit ("hook") control, to lack of wrist control and high frictional forces associated with the cable and hook hardware resulting in extreme complexity, to burdensome maintenance, to questionable reliability, and to exorbitant cost associated with bionic methodology.

Unfortunately, the prior methods and apparatus used in association with the control of prostheses tend to have the common disadvantage that the control devices are unproportionately large in size for the number of modes of motion the artificial limb is expected to produce. Similarly, numerous methods have been proposed for the discrimination of control signals used for causing artificial limbs to produce various motions. Such methods and apparatus have, for example, used a plurality of independent input devices, prescribed voice sounds uttered by the user as instruction signals, bioelectric signals for controlling the motion, feedback circuits for controlling the motion, complicated models, mini-central processing units, varying a cutoff frequency, the use of mechanical structures such as springs and associated stepping motors to simulate finger and wrist motion, and related pressure devices to assist in controlling prostheses.

It is known that most prosthetic limb devices are clumsy, have severe motion limitations, and are unnatural in appearance. Nonetheless, remote manipulators bearing similarities to the forearm and hand have been used in space, planetary exploration, deep-sea work and nuclear research. Most such devices suffer from a high cost, lack of controllability and an inability to reproduce human limb motions. Most remote manipulators of the foregoing types, including the prosthetic devices are unable to perform typical motions without including significant equipment. Developers have approached the problem along two separate fronts. First, the typical approach is not to use wrist motion at all. Such an approach can be recognized by the use of a claw or hook-type prosthetic. The claw or hook must be rotated about an axis of the arm to align the claw or hook with the object to be grasped. Typically, the prior motion must be followed by orienting the arm such that the object picked up can be held at an acceptable angle relative to vertical. Second, when wrist motion is necessary and the size, weight and cost are not constraints, a gimbaled, azimuth/elevation-type wrist joint has been used. A two degree of freedom gimbaled wrist manipulator can duplicate the total wrist motion. Even then, with a two degree of freedom gimbaled arrangement, the required placement of drive motors and control devices for this type of manipulator results in a rather large and bulky package.

Artificial limbs are readily attached to a shoulder socket or upper arm. Typically the most favored prosthesis is one which uses the "shrug" control. A shrug-type controller typically includes a hook and cable system which was originally developed in the 1800's. Such systems have only two digit control, lack wrist control and have high frictional forces with respect to the cable and hook hardware. Further, such hardware is complex, difficult to maintain, not reliable and expensive. Nonetheless, the hook and cable, shrug control method is still widely favored by below-the-elbow-amputees. Reasons cited for the widely favored acceptance of shrug control devices include the low cost, the ease of repair, the reliability and the simple pretension of the hook derived from the shoulder/back muscle through a harness and cable assembly.

Typically, such prostheses have a shoulder socket placed on the shoulder stump comprising an elbow joint operated by rods and connected to the shoulder socket, a forearm socket pivotally attached to an elbow joint and provided means for rotating the forearm, and an artificial hand complete with moveable fingers united with the forearm socket. Movements of the arm at the elbow joint and the opening and closing of the fingers are carried out with respect to such prostheses by the aid of the movement of the rods.

Obviously, movement by means of such artificial limbs requires great effort by the wearer of the arm. These efforts are particularly great when opening and closing the fingers of an artificial hand. Further, the possibility of making these-movements-restricted as they-are, can be performed only in a number of certain positions of the stump (prostheses). The process of transmitting these efforts from the shoulder and other parts of the body by the aid of rods is very uncomfortable and requires complex and unsightly movements.

Although many prosthetic devices have been developed, one system widely favored by below-the-elbow-amputees is a variation of the "hook and cable system." Reasons for the preferred use of the hook and cable system, cited by experts in this field include low costs, easy repair, reliability, and simple pretension of the hook derived from the shoulder/back muscle through the harness cable assembly.

The advantages of the present invention over the prior devices include: the easy to use "shrug" techniques to generate discrete finger digit control and wrist rotation; the compactness with which the control system can be easily mounted in the body of the prosthetic device; conformal printed circuit type conductors can be employed; improved maintenance; individual finger digit control is proposed instead of hook with cable actuation; wrist rotation capability; hardware programmable; lower cost than conventional prostheses and the use of frictional forces for actuation.

The present invention facilitates easy adaptation by either child or adult users, compensating for the "shrug" distance adjustable by the potentiometer. The "shrug" control envelope may be linear or logarithmic as determined by the integrated circuit selection. The electronic control package of the present invention is quite small in comparison to the prior devices. The electronic control package of the present invention is easily mounted in the prosthetic device and requires no additional containers or carriers to be worn by the user.

Primary to the present invention is the combination of the well known concept of control of prosthetic devices to the application of prosthetic arms. This combination results in improved finger and wrist control of the prostheses using a bar graph driver for simple, inexpensive generation of discrete control signals for discriminating and calibrating signals to establish multiple control routines.

It is, therefore, a feature of the present invention to provide a prostheses control system and method which in normal use provides for sequential or specific control of each finger digit, for wrist rotation or the like from signals derived from a transducer actuated by shoulder/back muscle movement.

A feature of the present invention is to provide the user with a "shrug" technique apparatus and method to generate discrete digit and wrist movement.

Another feature of the present invention is to provide a control system that can be easily mounted in the body of the prosthetic device.

Yet another feature of the present invention is to provide novel sensing and electronic control techniques.

Still another feature of the present invention is to provide a high level signal using typical shrug techniques.

Still another feature of the present invention is to provide individual finger digit control with a "shrug"-technique-as opposed to a "hook" with cable actuation.

Still another feature of the present invention is to provide for individual finger digit control at the same time as wrist rotation capability.

Still another feature of the present invention is to provide hardware programmable prostheses.

Still another feature of the present invention is to provide a low cost prostheses control system.

Still another feature of the present invention is to provide low frictional forces for actuation of the prostheses control system.

Additional features and advantages of the invention will be set forth in part in the description which follows, and in part will become apparent from the description, or may be learned by practice of the invention. The features and advantages of the invention may be realized by means of the combinations and steps particularly pointed out in the appended claims.

STATEMENT OF THE INVENTION

To achieve the foregoing objects, features and advantages and in accordance with the purpose of the invention as embodied and broadly described herein, a control system for use with a prosthetic device is provided. The prosthetic device comprises a plurality of moveable sub-prostheses and incorporates an implementation of the well known harness-and-shoulder control hardware such that the conventional shoulder shrug control movement associated with a moveable body part ranging from the no-shrug position of the moveable body part through the full-shrug position of the moveable body part provides control by the user to the prosthetic-device. The control system comprises (a) a transducer for receiving the movement from the body part-and-for generating a sensing signal in association with the movement of the body part, (b) a linearizer for linearizing the sensing signal received from the transducer to be a linear function of the magnitude of the distance moved by the body part, (c) a normalizer for normalizing the linear signal received from the linearizer to be a function of the entire range of body part movement from the no-shrug position of the moveable body part through the full-shrug position of the moveable body part, (d) a discriminator for dividing the normalized signal received from the normalizer into a plurality of discrete command signals, and (e) a converter connected to the prosthetic device for receiving the discrete command signals and driving the respective moveable sub-prostheses of the prosthetic device. Further, the present invention provides that the discrete command signals may be sustained linear commands, unsustained linear commands, sustained logarithmic commands or unsustained logarithmic commands. Still further, the respective logarithmic commands can be sequential or non-sequential, and similarly, the linear commands can be sequential or non-sequential.

In another embodiment of the present invention, a control system for use with a prosthetic device is provided. The prosthetic device comprises a plurality of moveable sub-prostheses and incorporates an implementation of the well known harness-and-shoulder control hardware such that the conventional shoulder shrug control movement associated with the moveable body part ranging from the no-shrug position of the moveable body part through the full-shrug position of the moveable body part provides control by the user to the prosthetic-device, wherein-the control system comprises (a) a shoulder harness for engaging the body part and for receiving and modifying the movement from the body part, (b) a linear potentiometer for receiving the movement from the shoulder harness and for generating a linear sensing signal in consonance with the movement of the body part, (c) an attenuator potentiometer for receiving the linear signal from the linear potentiometer-and-for scaling the linear signal to be a function of the entire range of body part movement from the no-shrug position of the moveable body part through the full-shrug position of the moveable body part, (d) a bar graph driver for receiving the scaled linear signal from the attenuator potentiometer-and for dividing the scaled signal into a plurality of discrete command signals, (e) a current driver for receiving the discrete command signals from the bar graph driver and for generating drive signals, and (f) a solenoid/motor arrangement in operational association with the prosthetic device for receiving the drive signals from the current driver and controlling the respective moveable sub-prostheses-of the prosthetic device.

In yet another embodiment of the present invention a method is provided for controlling a prosthetic device. The method of controlling the prosthetic device is associated with a prosthetic device comprising a plurality of moveable sub-prostheses in association with an implementation of the well known harness and shoulder control hardware such that the conventional shoulder shrug control movement associated with a moveable body part ranging from the no-shrug position of the moveable body part through the full-shrug position of the moveable body part provides control by the user to the prosthetic device. The method for controlling this prosthetic device comprises the steps of receiving the movement from the body part, generating a sensing signal in-consonance-with the movement of the body part, linearizing the sensing signal to be a linear function of the magnitude of the distance moved by the body part, normalizing the linear signal to be a function of the entire range of body movement from the no-shrug position of the moveable body part through the full-shrug position of the moveable body part, dividing the normalized signal into a plurality of discrete command signals, and implementing the plurality of discrete command signals for driving the respective moveable sub-prostheses of the prosthetic device.

BRIEF DESCRIPTION OF THE DRAWINGS

The accompanying drawings which are incorporated in and constitute a part of the specification, illustrate a preferred embodiment of the invention and together with the general description of the invention given above and the detailed description of the preferred embodiment given below, serve to explain the principles of the invention.

The above general description and the following detailed description are merely illustrative of the generic invention, and additional modes, advantages, and particulars of this invention will be readily suggested to those skilled in the art without departing from the spirit and scope of the invention.

DETAILED DESCRIPTION OF THE INVENTION

Reference will now be made in detail to the present preferred embodiments of the invention as described in the accompanying drawings.

Figure 1:
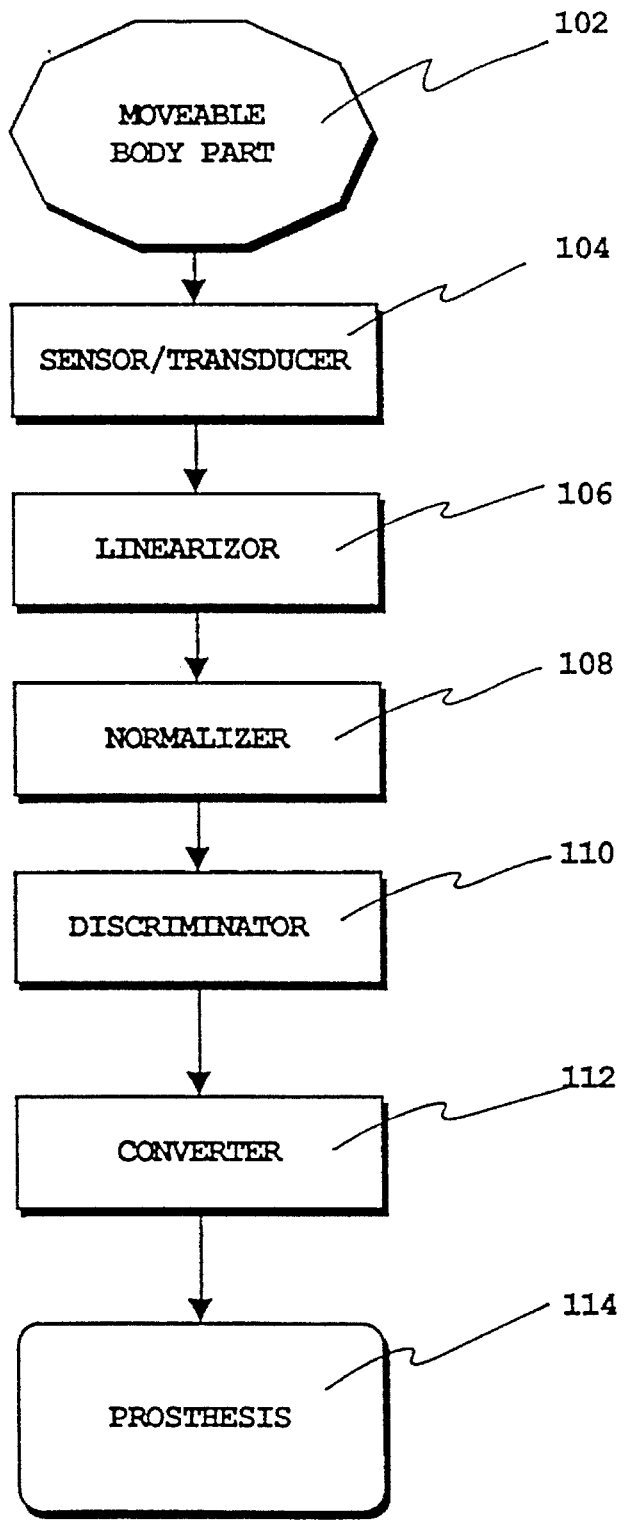
FIG. 1 is a flow diagram illustrating one embodiment of the control system for prosthetic devices of the present invention.

FIG. 1 is a schematic of a preferred embodiment of the present invention illustrating a control system for prosthetic devices. The prosthetic device utilized with the present invention has a plurality of moveable sub-prostheses. The prosthetic device, and its plurality of moveable sub-prostheses, incorporates the implementation of the well known harness-and-shoulder control hardware. The well known harness-and-shoulder control hardware provides that the conventional shoulder shrug control movement associated with a moveable body pan can be used. The moveability of the body part ranges from a no-shrug position through a full-shrug position. The relative movement of the user's body part provides control for the user to the prosthetic device.

The control system of the present invention, illustrated in FIG. 1, comprises generally a sensor/transducer 104, a linearizer 106, a normalizer 108, a discriminator 110, a converter 112 in operative association with the moveable body part 102 and the prosthesis 114. The sensor/transducer 104 engages the moveable body part 102. The transducer 104 generates a sensing signal operatively associated with the movement of the body part 102. The sensing signal generated by the transducer 104 is applied to the linearizer 106. The linearizer 106 linearizes the sensing signal to create a linear function of the magnitude of the distance moved by the body part 102. The linearized signal from the linearizer 106 is provided to the normalizer 108. The normalizer 108 normalizes the linear signal to be a function of the entire range of body part 102 movement from a no-shrug position through the full-shrug position of the individual user. The normalized signal created by the normalizer 108 is provided to the discriminator 110. The discriminator 110 divides the normalized signal into a plurality of discrete command signals. The discrete command signals created by the discriminator 110 are provided to the converter 112. The converter 112 is in operational association with the prosthetic device 114. The converter 112 receives the discrete command signals from the discriminator 112 and uses the signals for driving the respective moveable sub-prostheses 114 of the prosthetic device.

Figure 2:
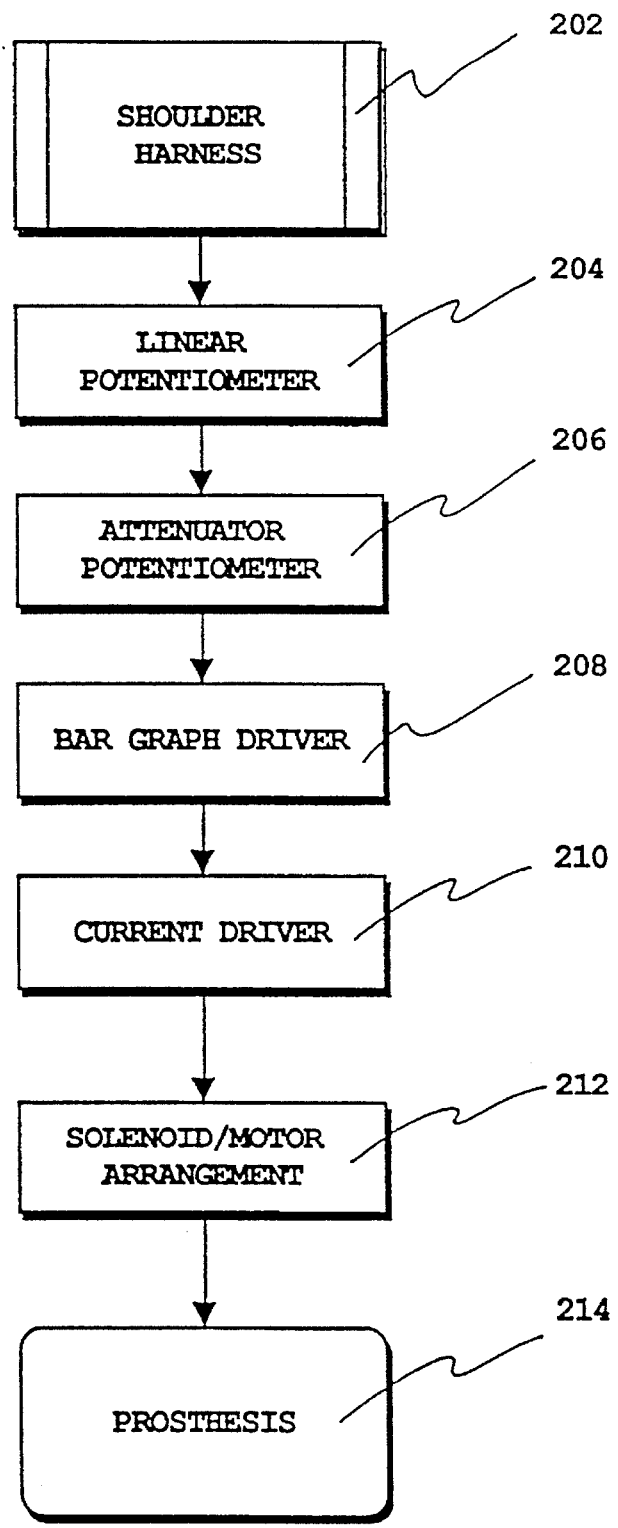
FIG. 2 is a flow diagram of another embodiment of the control system for prosthetic devices of the present invention.

FIG. 2 is a flow diagram illustrating another embodiment of the control system for prosthetic devices associated with the present invention. The primary elements of the embodiment of the control system illustrated in FIG. 2 are a shoulder harness 102, a linear potentiometer 204, an attenuator potentiometer 206, a bar graph driver 208, a current driver 210, a solenoid/motor arrangement 212 and a prosthesis 214. As with the prior embodiment, the prosthetic device has a plurality of sub-prostheses. Further, the prosthetic device incorporates an implementation of the well known harness-and-shoulder control hardware such that the conventional shoulder shrug control movement associated with a moveable body part can range from the no-shrug position to the full-shrug position of the moveable body part. The movement of the body part provides control by the user to the prosthetic device 214. The control system illustrated in FIG. 2 comprises the shoulder harness 202 for directly engaging the moveable body part and for receiving the movement therefrom. The body movement from the shoulder harness 202 is applied to the linear potentiometer 204. The linear potentiometer 204 generates a linear sensing signal in consonance with the movement of the shoulder harness 202. The linear sensing signal of the potentiometer 204 is applied to the attenuator potentiometer 206. The attenuator potentiometer 206 scales the linear sensing signal. Preferably, the scaling applied by the attenuator potentiometer 206 provides a function of the entire range of body part movement from the no-shrug position of the moveable body part to the full-shrug position of the moveable body part. The scaled linear signal from the attenuator potentiometer 206 is applied to the bar graph driver 208. The bar graph driver 208 divides the scaled signal into a plurality of discrete command signals. The discrete command signals are used by the current driver 210 for generating drive signals. The drive signals generated by the current driver 210 are applied to the solenoid or motor arrangement 212. The motor arrangement 212 is in operational association with the prosthetic device 214. The prosthetic device receives the drive signals from the motor arrangement 212 as provided by the current driver 210.

Figure 3:
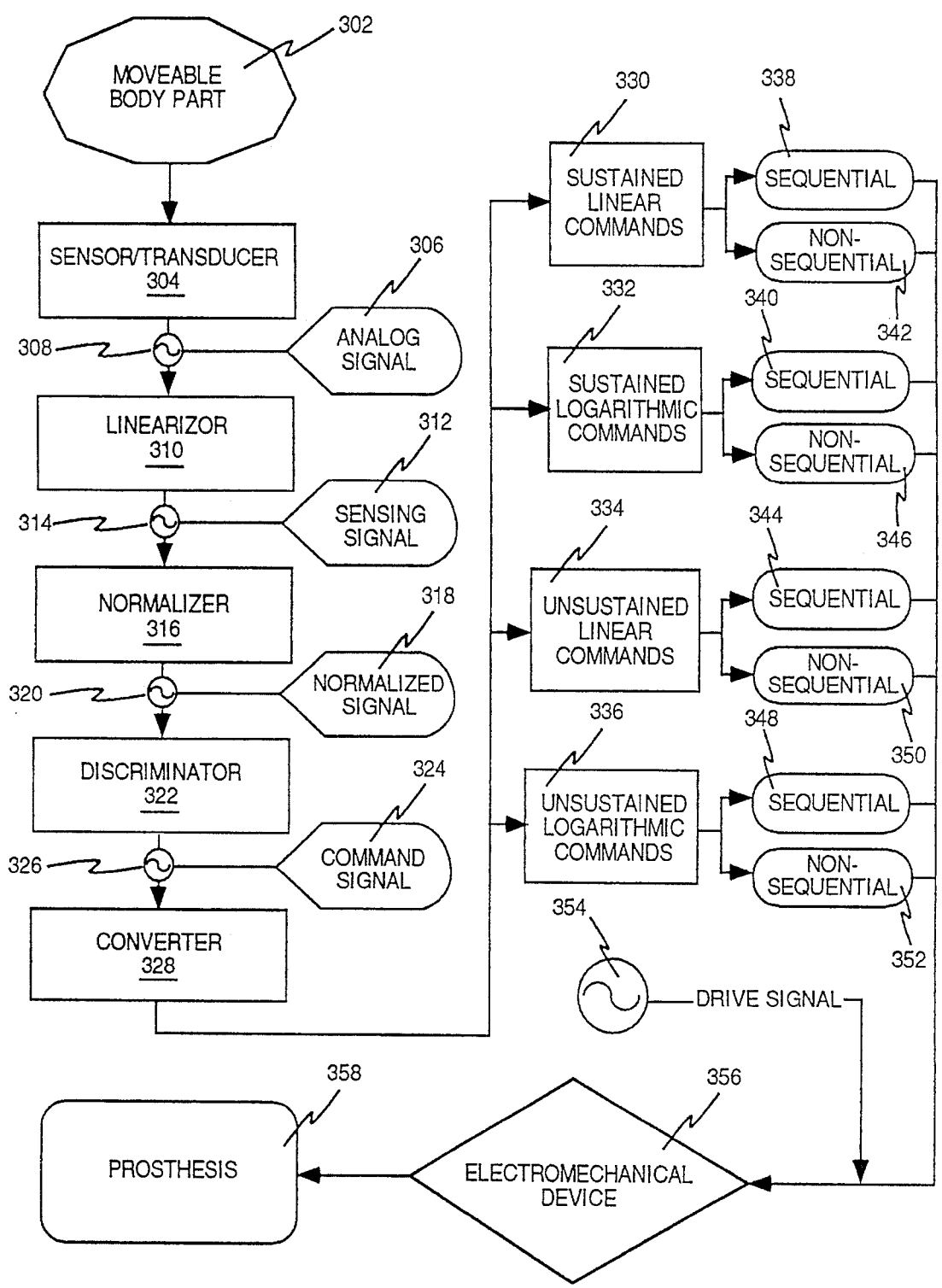
FIG. 3 is a detailed schematic of one embodiment of the present invention illustrating a control system for prosthetic devices.

FIG. 3 illustrates a more detailed version of yet another embodiment of the present invention. FIG. 3 is quite similar to FIG. 1, but includes more specificity with respect to variations on acquiring an appropriate drive signal for a prosthesis 358 in association with a moveable body part 302. A moveable body part 302 provides motion which is detected by a transistor 304. The sensor/transducer 304 provides an analog signal 306. The analog signal 306 is provided via a line 308 to a linearizer 310. The linearizer 310 creates a linear sensing signal 312. The linear sensing signal 312 is provided via a line 314 to a normalizer 316. The normalizer 316 provides a normalized signal 318. The normalized signal 318 is provided via a line 320 to a discriminator 322. The discriminator 322 generates specific command signals 324. The command signals 324 are provided via a line 326 to a converter 328. The converter provides four distinct options: the command signals can be sustained linear commands 330, sustained logarithmic commands 332, unsustained linear commands 334 or unsustained logarithmic commands 336. The sustained linear commands 330 can be sequential commands 338 or non-sequential commands 342. The sustained logarithmic commands 332 can be sequential commands 340 or non-sequential commands 346. Similarly, the unsustained linear commands 334 can be sequential commands 344 or non-sequential commands 350. And lastly, the unsustained logarithmic commands 336 can be either sequential commands 348 or non-sequential commands 352. The respective commands are provided to an electromechanical device 356 in association with a drive signal 354. The electromechanical device 356 is in operational association with the prosthesis 358.

Figure 4:
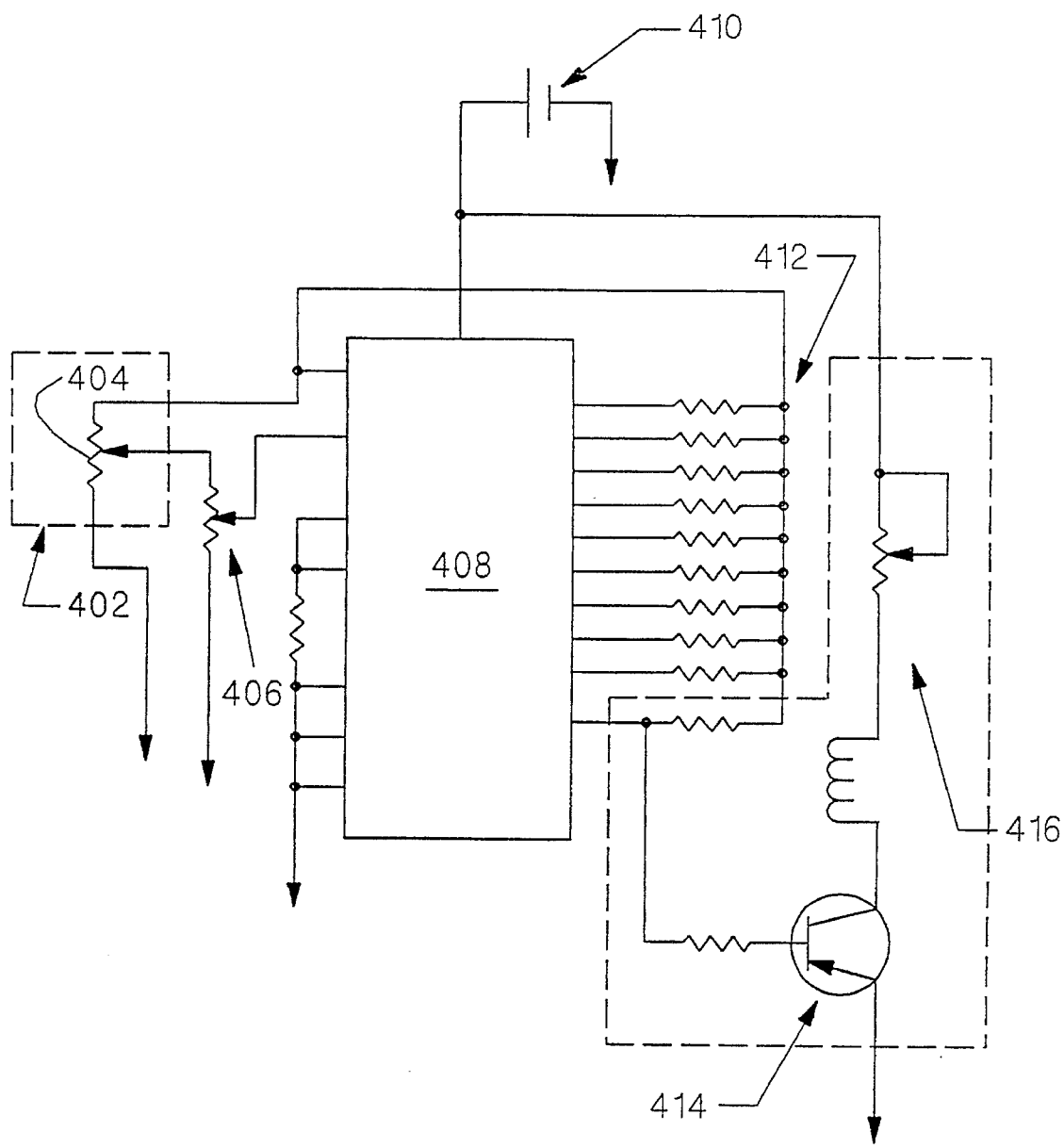
FIG. 4 is a schematic view of a preferred embodiment of the control system for prosthetic devices associated with the present invention.

FIG. 4 illustrates a schematic view of one embodiment of the control system for prosthetic devices of the present invention. The invention illustrated in FIG. 4 also employees the favored harness-and-shoulder shrug control. It should be noted that the shoulder hardware does not include mechanical portions as does prior used devices. A shoulder harness 402 incorporates a powered linear potentiometer 404. The linear potentiometer 404 generates a linear electrical signal in working relationship with the conventional shoulder shrug control movement. The linear signal is provided to an attentuator potentiometer 406. The attenuator potentiometer 406 facilitates the scaling of shoulder physical movement with the electrical sensing signal. The scaling accommodates various users. For example, children or elderly persons with less shoulder shrug capability can function just as easily as users with great flexibility in shoulder shrug capability. Thus, for example, some individuals might only be able to create a one inch "shrug" whereas other users might be able to force a three inch "shrug." The attenuator potentiometer 406 is adjusted to a desired electrical output, for example, one volt for a full shrug. An analog signal is created and fed to a bar graph driver 408 which receives electrical power from battery 410. The bar graph driver 408 converts the analog input signal from a zero shrug to a full shrug via a plurality of discrete sustained sequential linear commands. For example, ten discrete commands might be appropriate. Alternately, the bar graph driver 408 can convert the analog input signal to a plurality of sustained sequential logarithmic digital commands. Yet still another alternative for use with the bar graph driver 408 is to provide a "dot" mode of operation of the bar graph driver. Thus, discrete nonsustained digital commands can also be generated. By cascading two bar graph drivers, outputs comprising twenty discrete command signals may be obtained. It is obvious to one skilled in the art that additional cascading is possible.

Each of the outputs from the ports of the bar graph driver 408 are fed into a current driver 414 via a different respecitve one of a group sinking current limiting resisters of a plurality of sinking current limiting resisters 412. The current driver 414 drives a solenoid or other arrangement 416. The arrangement 416 results in finger movement in, for example, a sequential manner such that with a no shrug, all fingers would be in the extended position. As the "shrug" begins, the thumb and fingers would move sequentially to the closed position. All of the discrete commands may not be required. See, for example, FIG. 5. As another example, the "shrug" transducer may be located on the right shoulder for finger digit control and a duplicate system can be mounted on the left shoulder for providing wrist rotation control. The wrist rotation control can be adapted by using a stepping motor located at the wrist which incorporates a plurality of steps received via the bar graph driver 408. Yet still another preferred embodiment of the present invention provides that one or more of the digital commands, or other selected steps equating to a full "shrug" could be used as a "home" or reset command. Thus, simultaneously, all the fingers will return to a specific configuration. Therefore, fingers which may have been "shrugged" to a gripping position would move back to the extended position when the home or reset command is engaged.

It is appreciated by those skilled in the art that the control system of the present invention can be used on any device requiring signal translation, analog or otherwise. The analog signal translation can encompass either linear or logarithmic discrete commands, and progressive commands, and include homing capabilities. Further, an audible tone can be generated by each discrete command to provide further feedback for finger or wrist positions via, for example, earphone feedback.

Figure 5:
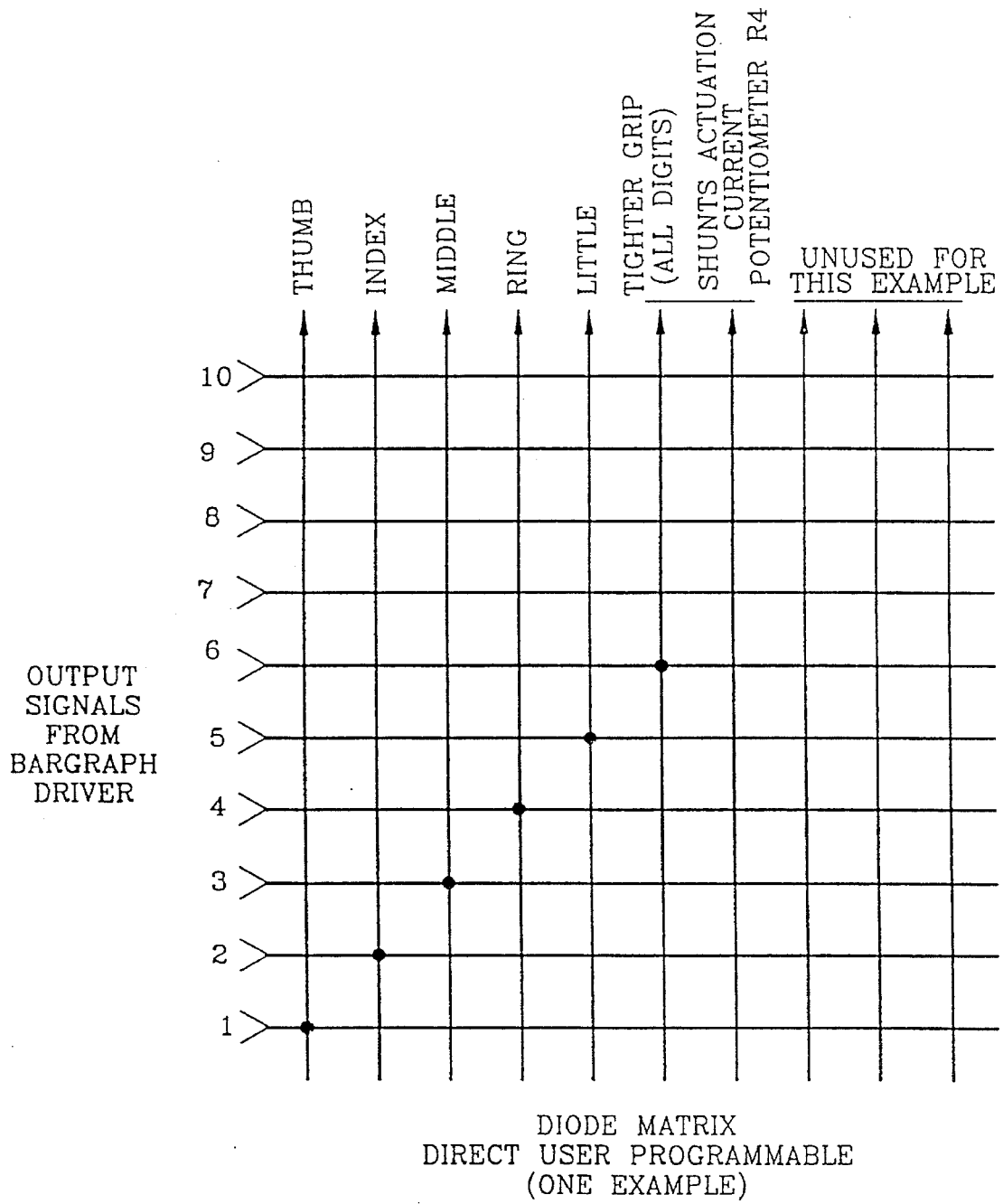
FIG. 5 is a drawing illustrating the versatility of the present invention with respect to individual users.

FIG. 5 illustrates the control signals associated with a digit and wrist control mechanism. The respective diode matrix can be directly programmed by the user. The output signals from the bar graph device are provided on the abscissa and the digits and gripping information are provided along the ordinate.

A method for controlling a prosthetic device is also provided in association with the present invention. The method for controlling the prosthetic device comprises the steps of receiving the movement from the body part, generating a sensing signal in consonance with the movement of the body part, linearizing the sensing signal to be a linear function of the magnitude of the distance moved by the body part, normalizing the linear system to be a function of the entire range of body part movement from the no-shrug position of the moveable body part through the full-shrug position of the moveable body part, dividing the normalized signal into a plurality of discrete command signals, and implementing the plurality of discrete command signals for driving the respective moveable sub-prostheses of the prosthetic device.

Additional advantages and modification will readily occur to those skilled in the art. The invention in its broader aspects is therefore not limited to the specific details, representative apparatus, and the illustrative examples shown and described herein. Accordingly, the departures may be made from the details without departing from the spirit or scope of the disclosed general inventive concept.

What is claimed is:

1. A method for controlling a prosthetic device, the prosthetic device comprising a plurality of moveable sub-prostheses and incorporating any implementation of harness and shoulder control hardware such that the shoulder shrug control movement associated with a moveable body part ranging from the no-shrug position of the moveable body part through the full-shrug position of the moveable body part provides control by the user to the prosthetic device, the method for controlling the prosthetic device comprising the steps of:

(a) receiving the movement from the body part, (b) generating a sensing signal in consonance with the movement of the body part, (c) linearizing the sensing signal to be a linear function of the magnitude of the distance moved by the body part, (d) normalizing the linear signal to be a function of the entire range of body part movement from the no-shrug position of the moveable body part through the full-shrug position of the moveable body part, (e) dividing the normalized signal into a plurality of discrete command signals, and (f) implementing the plurality of discrete command signals for driving a respective one of said plurality of moveable sub-prostheses of the prosthetic device.

2. A method for controlling a prosthetic device as defined in claim 1 wherein said step of dividing the normalized signal into a plurality of discrete command signals further comprises providing sustained linear commands.

3. A method for controlling a prosthetic device as defined in claim 2 wherein the step of providing sustained linear commands further comprises the step of dispensing sequential sustained linear commands.

4. A method for controlling a prosthetic device as defined in claim 2 wherein the step of providing sustained linear commands further comprises the step of dispensing non-sequential sustained linear commands.

5. A method for controlling a prosthetic device as defined in claim 1 wherein said step of dividing the normalized signal into a plurality of discrete command signals further comprises providing unsustained linear commands.

6. A method for controlling a prosthetic device as defined in claim 5 wherein the step of providing unsustained linear commands further comprises the step of dispensing sequential unsustained linear commands.

7. A method for controlling a prosthetic device as defined in claim 5 wherein the step of providing unsustained linear commands further comprises the step of dispensing non-sequential unsustained linear commands.

8. A method for controlling a prosthetic device as defined in claim 1 wherein said step of dividing the normalized signal into a plurality of discrete command signals further comprises providing sustained logarithmic commands.

9. A method for controlling a prosthetic device as defined in claim 8 wherein the step of providing sustained logarithmic commands further comprises the step of dispensing sequential sustained logarithmic commands.

10. A method for controlling a prosthetic device as defined in claim 8 wherein the step of providing sustained logarithmic commands further comprises the step of dispensing non-sequential sustained logarithmic commands.

11. A method for controlling a prosthetic device as defined in claim 1 wherein said step of dividing the normalized signal into a plurality of discrete command signals further comprises providing unsustained logarithmic commands.

12. A method for controlling a prosthetic device as defined in claim 11 wherein the step of providing unsustained logarithmic commands further comprises the step of dispensing sequential unsustained logarithmic commands.

13. A method for controlling a prosthetic device as defined in claim 11 wherein the step of providing unsustained logarithmic commands further comprises the step of dispensing non-sequential unsustained logarithmic commands.

* * * * *